(12) United States Patent
Lin et al.

(10) Patent No.: US 8,965,100 B2
(45) Date of Patent: Feb. 24, 2015

(54) ULTRASONIC MODELING FOR INSPECTION OF COMPOSITE IRREGULARITIES

(75) Inventors: John Z. Lin, Renton, WA (US); Hong Tat, Redmond, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 212 days.

(21) Appl. No.: 13/355,100

(22) Filed: Jan. 20, 2012

(65) Prior Publication Data

US 2013/0188858 A1 Jul. 25, 2013

(51) Int. Cl.
*G06K 9/00* (2006.01)
(52) U.S. Cl.
USPC ........... 382/141; 382/144; 382/145; 382/149; 382/286; 382/291; 382/152
(58) Field of Classification Search
CPC .................. G06T 7/0004; G06T 2207/30108; G06T 2207/10132; G06T 2207/10136
USPC .......... 382/141, 144, 145, 149, 286, 291, 152
See application file for complete search history.

(56) References Cited

U.S. PATENT DOCUMENTS

| | | | |
|---|---|---|---|
| 4,412,315 A | 10/1983 | Flournoy | |
| 4,461,178 A | 7/1984 | Chamuel | |
| 5,404,755 A | 4/1995 | Olson et al. | |
| 5,554,808 A | 9/1996 | Chiao | |
| 5,619,587 A * | 4/1997 | Willoughby et al. | 382/141 |
| 6,637,266 B1 * | 10/2003 | Froom | 73/583 |
| 6,856,918 B2 | 2/2005 | Dubois et al. | |
| 7,467,052 B2 | 12/2008 | Vaccaro | |
| 7,584,062 B1 * | 9/2009 | Tat et al. | 702/39 |
| 7,822,258 B2 * | 10/2010 | Senibi et al. | 382/141 |
| 2003/0154801 A1 * | 8/2003 | Georgeson | 73/799 |
| 2004/0031337 A1 * | 2/2004 | Masaniello et al. | 73/865.8 |
| 2005/0102109 A1 * | 5/2005 | Dubois et al. | 702/39 |
| 2005/0241397 A1 * | 11/2005 | Bergman | 73/606 |
| 2010/0126277 A1 * | 5/2010 | Wu et al. | 73/602 |
| 2010/0329081 A1 * | 12/2010 | Sullivan et al. | 367/120 |

OTHER PUBLICATIONS

Miencazkowski, M., et al.; Modeling of Ultrasonic Wave Propagation in Composite Airframe Components; Review of Quantitative Nondestructive Evaluation; 2008; pp. 995-1001; vol. 27; American Institute of Physics.
Smith, R. A., et al.; Automated Non-Destructive Analysis and Advanced 3D Defect Characterisation From Ultrasonic Scans of Composites; Presented at the 17th International Conference on Composite Materials; Jul. 27, 2009; Edinburgh.
UTSIM—Center for Nondestructive Evaluation; http://www.cnde.iastate.edu/ultrasonics/utsim; Copyright 2011 Center for NDE Iowa State University; 3 pages.
Image3D Ultrasonic Simulation; UTEX Scientific; http://www.utex.com; retrieved Jan. 20, 2012; 1 page.
CIVA: State of the Art Simulation Software for Non Destructive Testing; http://www-cive.cea.fr; ©CEA 2003-2012; 2 pages.
About PZFlex; http://www.pzflex.com; ©2011 Weidlinger Associates; 2 pages.

* cited by examiner

*Primary Examiner* — Mike Rahmjoo
(74) *Attorney, Agent, or Firm* — Armstrong Teasdale LLP

(57) ABSTRACT

A first simulated inspection is conducted to provide a first waveform data set associated with the at least one irregularity parameter. The first simulated inspection is conducted using a first evaluation setting. A first image is produced based on the first waveform set, and it is determined whether a quality of the first image satisfies a predetermined threshold.

20 Claims, 6 Drawing Sheets

| Input Parameters | Value | Unit | Material | Layup (Bottom Up) |
|---|---|---|---|---|
| Outer Ply Thickness (tf) = | | inch | | |
| Inner Ply thickness (t) = | | inch | Rayleigh Damping | |
| Number of plies (n) = | | | Alpha | |
| Total laminate Thickness (T) = | | inch | | |
| Max wrinkle height (H) = | | inch | Beta | |
| Wrinkle Width (W) = | | inch | | |
| Laminate Length (L) = | | inch | | |
| H^2/W= | | | | |
| Spacing for output points (Δx) = | | inch | | |
| Number of element layers per ply = | | For ABAQUS Element generation only | | |
| Area (Volume) Change = +/- 0.5H/T= | | | | |
| ABAQUS Element Type = | | | | |
| Source = | Pulse-Echo | | | |
| Source (Laser or Piezo) beam width = | | mm | Sensor Des. | |
| Source CL to Wrinkle CL Distance (d) = | | mm | Source | |
| Source to Receiver Span AS1= | | mm | Receiver | |
| Source to Receiver Span AS2= | | mm | Receiver | |
| Source to Receiver Span AS3= | | mm | Receiver | |
| Source to Receiver Span AS4= | | mm | Receiver | |
| Source to Receiver Span AS5= | | mm | Receiver | |
| Source to Receiver Span AS6= | | mm | Receiver | |
| Source Impulse Frequency | | MHz | B-Scan spacing (in.) | |
| Couplant | Water | | | |
| Couplant Height | | inch | | |
| Include Interface Resin Layers? | Yes | | | |
| Resin Interlayer Thickness(% of ply thick) | | | | |
| Resin Young's Modulus | | Msi | | |
| Resin Possion's Ratio | | | | |
| Resin Density | | lbs/in^3 | | |
| Create A-Scan Model | | Create B-Scan Model | | |

FIG. 7

ULTRASONIC MODELING FOR INSPECTION OF COMPOSITE IRREGULARITIES

BACKGROUND

The present disclosure relates generally to nondestructive evaluation of materials and, more particularly, to methods and systems for use in inspecting a composite structure for irregularities.

Known aircraft systems are increasingly being fabricated from composite materials. At least some structures fabricated from composite materials may include irregularities, such as wrinkles, formed during fabrication that may affect and/or alter a mechanical property of the composite material. As such, at least some structures fabricated from composite materials undergo nondestructive evaluation and/or inspection prior to installation and/or use.

One known method of inspecting such structures includes pulse-echo ultrasound and/or X-ray radiography. At least some such methods, however, only detect a shadow of the irregularity and, thus, a severity and/or a depth of the irregularity may not be fully characterized. Moreover, at least some such methods may be tedious and/or time consuming.

BRIEF SUMMARY

In one aspect, a method is provided for use in inspecting a composite structure. The method includes defining at least one irregularity parameter. A first simulated inspection is conducted to provide a first waveform data set associated with the irregularity parameter. The first simulated inspection is conducted using a first evaluation setting. A first image is produced based on the first waveform set, and it is determined whether a quality of the first image satisfies a predetermined threshold.

In another aspect, a computer-readable storage device is provided having encoded thereon computer readable instructions that are executable by a processor to perform functions including conducting a first simulated inspection to provide a first waveform data set associated with at least one irregularity parameter. The first simulated inspection is conducted using a first evaluation setting. A first image is produced based on the first waveform set, and it is determined whether a quality of the first image satisfies a predetermined threshold.

In yet another aspect, a system is provided. The system includes a modeling module that is configured to conduct a first simulated inspection to provide a first waveform data set associated with at least one irregularity parameter. The first simulated inspection is conducted using a first evaluation setting. An imaging module is configured to produce a first image based on the first waveform set, and determine whether a quality of the first image satisfies a predetermined threshold.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIG. 7 is a screenshot of an exemplary user interface that may be used to facilitate inspecting the composite structure shown in FIG. 2.

Although specific features of various embodiments may be shown in some drawings and not in others, this is for convenience only. Any feature of any drawing may be referenced and/or claimed in combination with any feature of any other drawing.

DETAILED DESCRIPTION

The subject matter described herein relates generally to nondestructive evaluation of materials and, more particularly, to methods and systems for use in inspecting a composite structure for irregularities. In one embodiment, a first simulated inspection is conducted to produce a first waveform data set associated with the at least one irregularity parameter. The first simulated inspection is conducted using a first evaluation setting, and a first image is produced based on the first waveform set. If the quality of the first image satisfies a predetermined threshold, the first evaluation setting is identified as a desired evaluation setting. As such, the first evaluation setting may be used to physically inspect the composite structure for irregularities, such as wrinkles.

An exemplary technical effect of the methods and systems described herein includes at least one of: (a) defining at least one irregularity parameter; (b) defining at least one composite structure parameter; (c) defining at least one stimulation parameter; (d) generating at least one model based on the at least one irregularity parameter; (e) conducting a first simulated inspection to provide a first waveform data set associated with at least one irregularity parameter; (f) determining whether a quality of the first image satisfies a predetermined threshold; and (g) identifying the first evaluation setting as a desired evaluation setting for use in inspecting the composite structure.

An element or step recited in the singular and proceeded with the word "a" or "an" should be understood as not excluding plural elements or steps unless such exclusion is explicitly recited. Moreover, references to "one embodiment" of the present invention and/or the "exemplary embodiment" are not intended to be interpreted as excluding the existence of additional embodiments that also incorporate the recited features.

Figure 1:
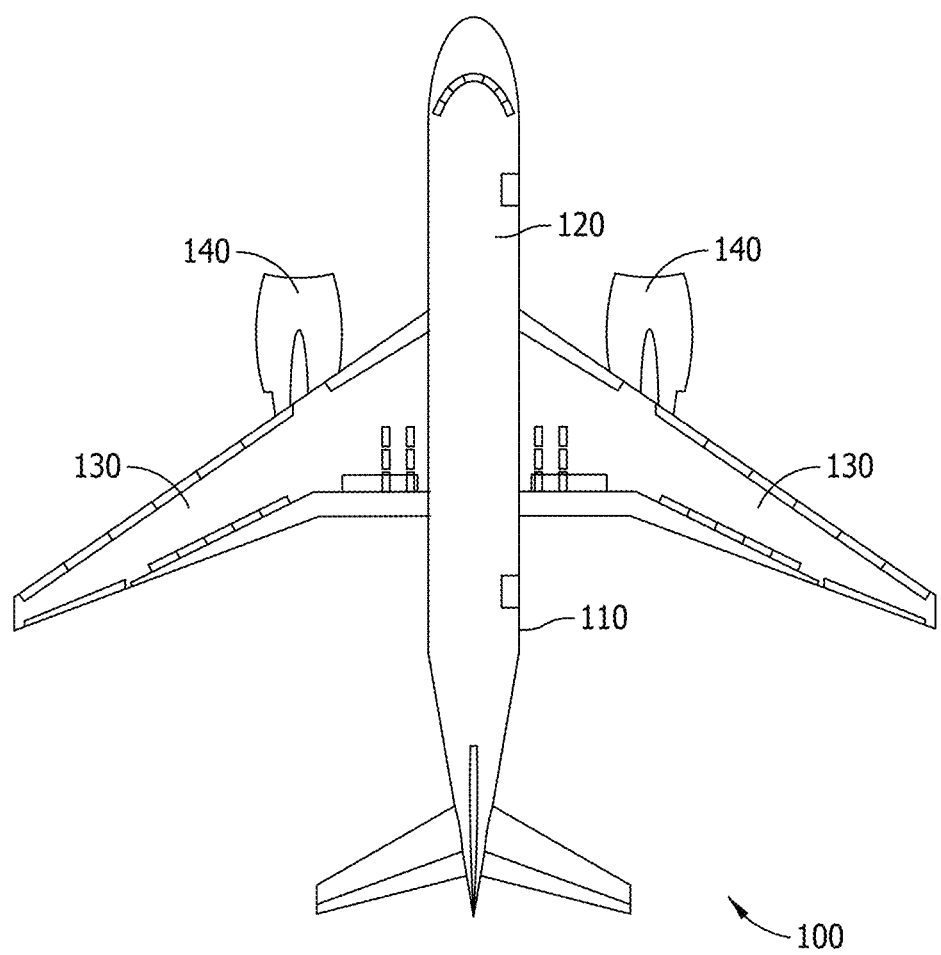
FIG. 1 is a plan view of an exemplary aircraft.

FIG. 1 is a plan view of an exemplary aircraft 100. In the exemplary embodiment, aircraft 100 includes a body 110 that includes a fuselage 120 and a pair of wings 130 extending from fuselage 120. In the exemplary embodiment, at least one engine 140 is coupled to each wing 130 to provide thrust to aircraft 100. Aircraft 100 may include any number of engines 140 that enables aircraft 100 to function as described herein. In the exemplary embodiment, aircraft 100 includes at least one component and/or structure that is fabricated from a composite material.

Figure 2:
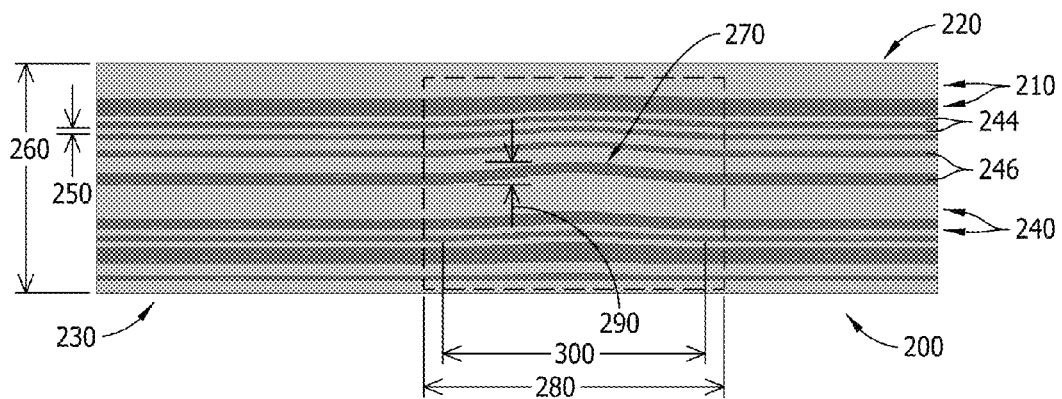
FIG. 2 is a cross-sectional view of an exemplary composite structure that may be used with the aircraft shown in FIG. 1.
Figure 3:
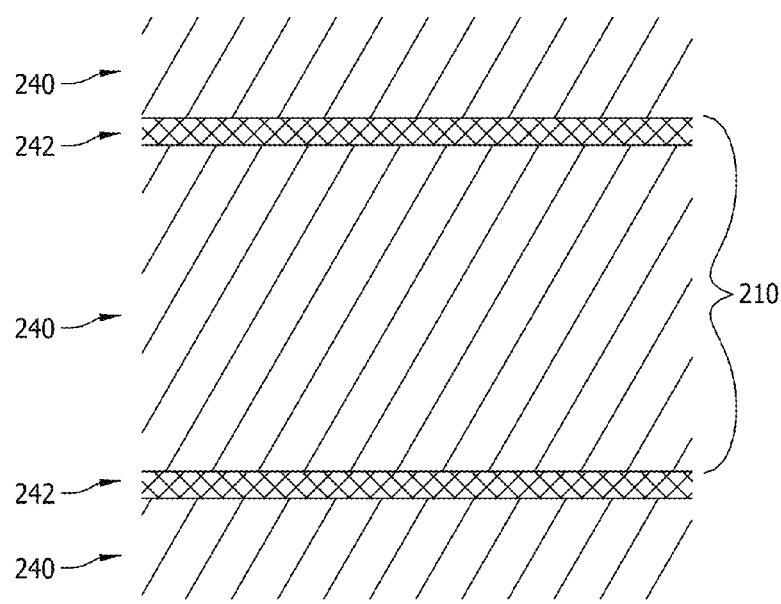
FIG. 3 is a detailed cross-sectional view of the composite structure shown in FIG. 2.

FIGS. 2 and 3 are cross-sectional views of a portion or coupon of an exemplary composite structure 200 that may be used with aircraft 100. In the exemplary embodiment, composite structure 200 includes a plurality of plies 210, a top surface 220, and a bottom surface 230. In the exemplary embodiment, each ply 210 includes a fiber-rich layer 240 and a resin layer 242 (not shown in FIG. 2). In the exemplary embodiment, resin layer 242 is generally disposed between adjacent fiber-rich layers 240.

In the exemplary embodiment, fiber-rich layers 240 include at least one first layer 244 and at least one second layer 246. In the exemplary embodiment, first layer 244 has fibers arranged in a first orientation, and second layer 246 has fibers arranged in a second orientation. Alternatively, fibers of each fiber rich layer 240 may be arranged in any orientation that enables the methods and systems to function as described herein.

In the exemplary embodiment, composite structure 200 has at least one composite structure parameter including an outer ply thickness (i.e., a thickness of an entire ply 210, including resin layer 242), an inner ply thickness (i.e., a thickness of fiber-rich layer 240), a number of plies, a ply layup, a composite structure thickness, a material used to fabricate at least a portion of the at least one composite structure, a resin thickness, and/or a resin density. For example, in the exemplary embodiment, each ply 210 has a thickness 250, and composite structure 200 has a total thickness 260 extending between top surface 220 and bottom surface 230.

A portion of structure 200 includes an irregularity 270 positioned between surfaces 220 and 230. That is, in the exemplary embodiment, plies 210 are not substantially uniform along a coupon length 280 of composite structure 200. In general, an $i^{th}$ ply distortion in an n-ply composite structure 200 may be described by a generic function of its bounding surfaces:

$$y_i'(x,y_i) = y_i + h(y_i)S(x), i=1,2,\ldots n+1 \quad \text{(Eq. 1)}$$

wherein $y_i$ is a non-distorted position of a ply surface, S(x) is an arbitrary shape function of the ply distortion, and $h(y_i)$ modulates the through-the-thickness severity of the distortion ($h(y_i)=0$ in non-distorted region). The x and y-coordinates represent the horizontal and vertical positions of a point in composite structure 200, respectively. More specifically, in the exemplary embodiment, irregularity 270 has at least one irregularity parameter including at least one of an irregularity thickness 290, an irregularity width 300, an irregularity length, an irregularity location, and an irregularity shape.

In the exemplary embodiment, irregularity 270 is positioned entirely within composite structure 200, such that a degree of irregularity 270 (e.g., irregularity thickness 290) is generally reduced near top surface 220 and/or a bottom surface 230 of composite structure 200. A two-dimensional cross-sectional area of a wrinkled $i^{th}$ ply may be calculated by:

$$\text{Area} = \int_{-w/2}^{w/2} [y'(x, y_{i+1}) - y'(x, y_i)] dx = \left[1 \pm \frac{H}{2T}\right] W_I \quad \text{(Eq. 2)}$$

wherein "+" is for the lower half of composite structure 200, and "−" is for the upper half of composite structure 200. Moreover, additional irregularity parameters may be expressed using:

$$h = \frac{H}{2}[1 - |2y/T|] \quad \text{(Eq. 3)}$$

$$y'(x, y) = y + \frac{h}{2}[1 + \cos(2\pi x/W)], \quad \text{(Eq. 4)}$$

$$\text{where} - \frac{W}{2} \le x \le \frac{W}{2}, -\frac{nt}{2} \le y \le \frac{nt}{2}$$

wherein H is the maximum irregularity thickness 290. Furthermore, density, elastic properties, and/or other material properties of composite structure 200 may also be adjusted according to a rule of mixtures where the changes in area are due to resin distribution. Alternatively, irregularity 270 may have any irregularity parameters that enable the methods and systems to function as described herein.

Figure 4:
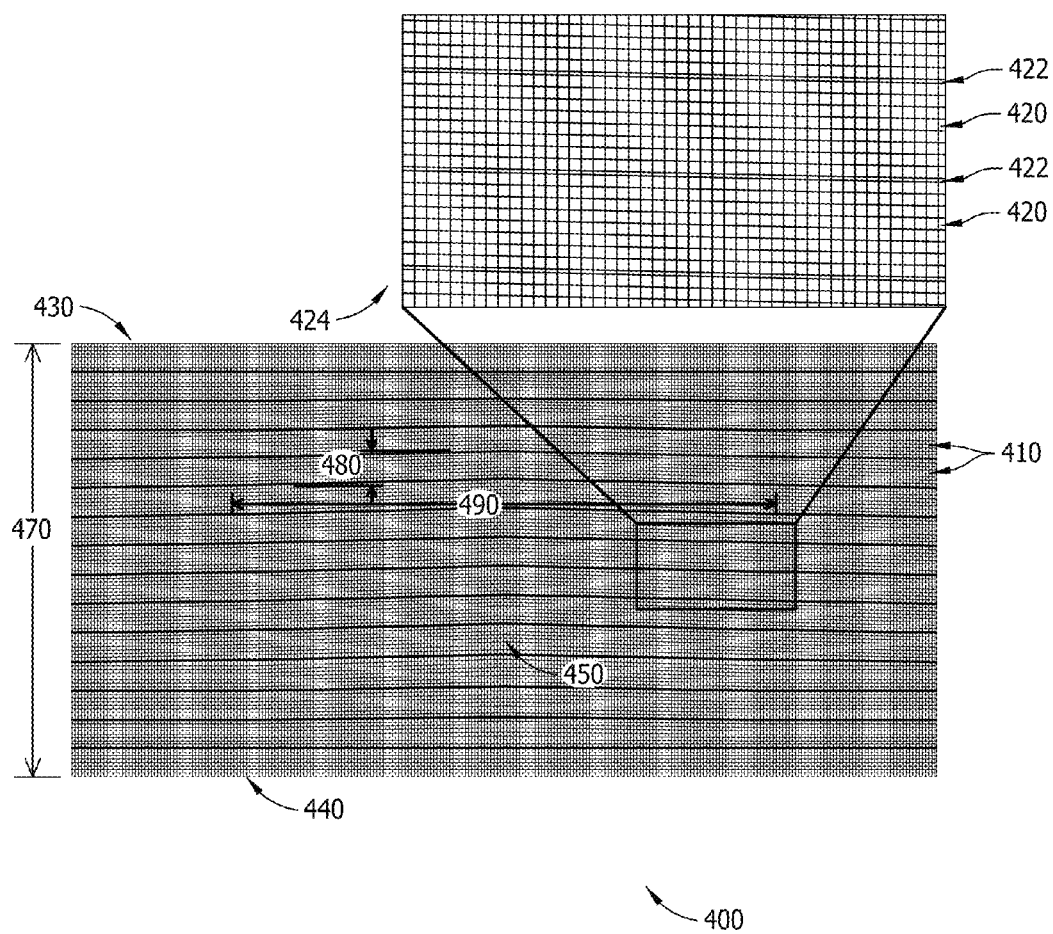
FIG. 4 is a model of the composite structure shown in FIGS. 2 and 3.

FIG. 4 is an exemplary model 400 of composite structure 200 (shown in FIGS. 2 and 3). That is, in the exemplary embodiment, model 400 is a virtual representation of each ply 210 (shown in FIGS. 2 and 3). More specifically, in the exemplary embodiment, model 400 includes a plurality of plies 410 that are associated with plies 210. In the exemplary embodiment, each ply 410 includes a fiber-rich layer 420 and a resin layer 422, as shown in insert 424.

In the exemplary embodiment, model 400 includes a top surface 430, a bottom surface 440, and an irregularity 450 positioned therebetween. In the exemplary embodiment, each ply 410 has a thickness 460, and model 400 has a total thickness 470 extending between top surface 430 and bottom surface 440. In the exemplary embodiment, irregularity 450 has at least one irregularity parameter including at least one of an irregularity thickness 480, an irregularity width 490, an irregularity length, an irregularity location, and an irregularity shape.

Figure 5:
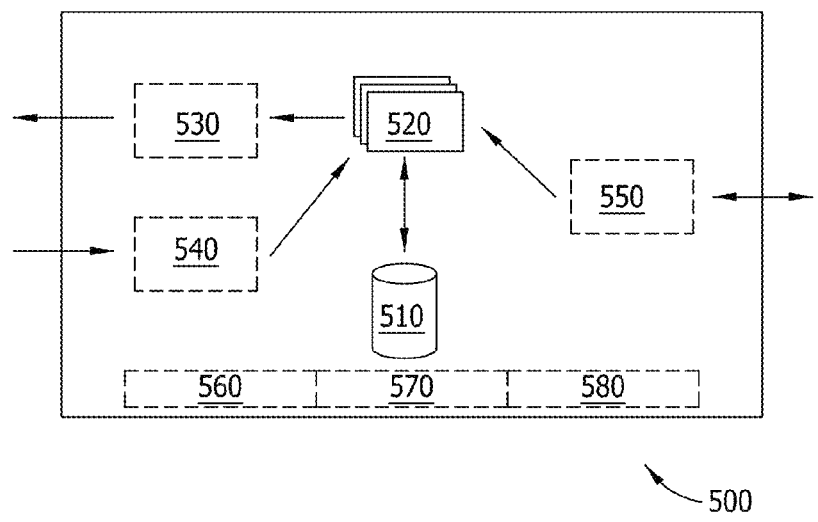
FIG. 5 is a schematic illustration of an exemplary computer system that may be used to inspect the composite structure shown in FIG. 2.

FIG. 5 is a schematic illustration of an exemplary computer system 500 that may be used to inspect composite structure 200 and/or irregularity 270. In the exemplary embodiment, computer system 500 includes a memory device 510 and a processor 520 coupled to memory device 510 for use in executing instructions. More specifically, in the exemplary embodiment, computer system 500 is configurable to perform one or more operations described herein by programming memory device 510 and/or processor 520. For example, processor 520 may be programmed by encoding an operation as one or more executable instructions and by providing the executable instructions in memory device 510.

Processor 520 may include one or more processing units (e.g., in a multi-core configuration). As used herein, the term "processor" is not limited to integrated circuits referred to in the art as a computer, but rather broadly refers to a controller, a microcontroller, a microcomputer, a programmable logic controller (PLC), an application specific integrated circuit, and other programmable circuits.

In the exemplary embodiment, memory device 510 includes one or more devices (not shown) that enable information such as executable instructions and/or other data to be selectively stored and retrieved. In the exemplary embodiment, such data may include, but is not limited to, properties of composite materials, properties of ultrasonic waves, modeling data, imaging data, calibration curves, operational data, and/or control algorithms. In the exemplary embodiment, computer system 500 is configured to automatically implement a parametric finite element analysis to determine a desired evaluation setting for use in inspecting composite structure 200 and/or irregularity 270. Alternatively, computer system 500 may be use any algorithm and/or method that enable the methods and systems to function as described herein. Memory device 510 may also include one or more computer readable media, such as, without limitation, dynamic random access memory (DRAM), static random access memory (SRAM), a solid state disk, and/or a hard disk.

In the exemplary embodiment, computer system 500 includes a presentation interface 530 that is coupled to processor 520 for use in presenting information to a user. For example, presentation interface 530 may include a display adapter (not shown) that may couple to a display device (not shown), such as, without limitation, a cathode ray tube (CRT), a liquid crystal display (LCD), a light-emitting diode (LED) display, an organic LED (OLED) display, an "electronic ink" display, and/or a printer. In some embodiments, presentation interface 530 includes one or more display devices.

Computer system 500, in the exemplary embodiment, includes an input interface 540 for receiving input from the user. For example, in the exemplary embodiment, input interface 540 receives information suitable for use with the methods described herein. Input interface 540 is coupled to processor 520 and may include, for example, a joystick, a keyboard, a pointing device, a mouse, a stylus, a touch sensitive panel (e.g., a touch pad or a touch screen), and/or a position detector. It should be noted that a single component, for example, a touch screen, may function as both presentation interface 530 and as input interface 540.

In the exemplary embodiment, computer system 500 includes a communication interface 550 that is coupled to processor 520. In the exemplary embodiment, communication interface 550 communicates with at least one remote device. For example, communication interface 550 may use, without limitation, a wired network adapter, a wireless network adapter, and/or a mobile telecommunications adapter. A network (not shown) used to couple computer system 500 to the remote device may include, without limitation, the Internet, a local area network (LAN), a wide area network (WAN), a wireless LAN (WLAN), a mesh network, and/or a virtual private network (VPN) or other suitable communication means.

In the exemplary embodiment, computer system 500 includes at least a modeling module 560, an imaging module 570, and an evaluating module 580 that enable the methods and systems to function as described herein. In the exemplary embodiment, modeling module 560 conducts a simulated inspection using a predefined evaluation setting to provide a waveform data set associated with at least one irregularity parameter. In the exemplary embodiment, modeling module 560 generates at least one model, as shown in FIG. 4, based on the at least one irregularity parameter. In the exemplary embodiment, at least one simulated ultrasound wave is transmitted towards the at least one model at a plurality of scanning positions, and at least one reflected and/or transmitted ultrasound wave is "detected" (i.e., projected and/or calculated by computer system 500) to facilitate providing the waveform data set. In the exemplary embodiment, the ultrasound waves may be transmitted towards and/or detected from any direction that enables the methods and systems to function as described herein.

Figure 6:
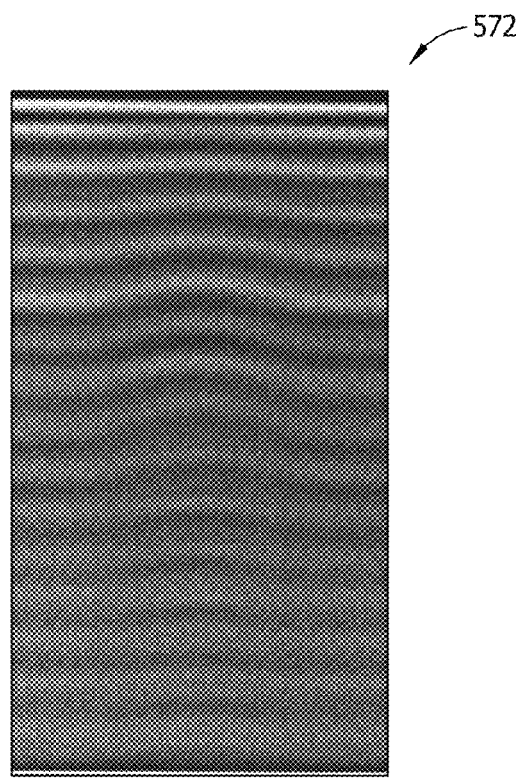
FIG. 6 is a screenshot of an exemplary virtual image of the model shown in FIG. 4.

In the exemplary embodiment, imaging module 570 produces an image based on the waveform set, and determines whether a quality of the image satisfies a predetermined threshold. FIG. 6 is a screenshot of a virtual image 572 of composite structure 200 produced by imaging module 570. If the quality of the image satisfies the predetermined threshold, in the exemplary embodiment, evaluating module 580 identifies the predefined evaluation setting as a desired evaluation setting for use in inspecting composite structure 200. If the quality of the image does not satisfy the predetermined threshold, in the exemplary embodiment, evaluating module 580 iteratively repeats the process using a finite element analysis until at least one desired evaluation setting is identified.

FIG. 7 is a screenshot of an exemplary user interface 600 that may be presented to a user on presentation interface 530. More specifically, in the exemplary embodiment, user interface 600 includes a plurality of fields 610 for use in providing data associated with modeling composite structure 200 and/or irregularity 270. For example, in the exemplary embodiment, fields 610 associated with modeling composite structure include at least an outer ply thickness, an inner ply thickness, a number of plies, a total laminate thickness, a ply layup (e.g., orientation of fiber rich layers 240), a material used to fabricate at least a portion of composite structure 200, a type of couplant, a couplant thickness, and/or material damping parameters. Moreover, in the exemplary embodiment, fields 610 associated with modeling irregularity 270 include at least a maximum irregularity thickness and/or a irregularity width. In addition to the aforementioned fields 610, in the exemplary embodiment, at least some fields 610 are associated with spacing for output points and/or a number of element layers per ply to enable each fiber-rich layer 240 and/or resin layer 242 to be precisely modeled. In the exemplary embodiment, the use of material properties may be dynamically obtained (e.g., in-plane velocity measurements) and may be used with an expandable material systems library (not shown).

Furthermore, in the exemplary embodiment, user interface 600 includes a plurality of fields 620 for use in providing data associated with an ultrasonic testing (UT) source or stimulating mechanism (not shown) and/or a stimulation of composite structure 200. For example, in the exemplary embodiment, fields 620 associated with the stimulating mechanism include at least a type of stimulation source, a stimulation source beam width, a distance between the at least one stimulating mechanism and the composite structure, a distance between the at least one stimulating mechanism and a sensor, and/or a stimulation source impulse shape and center frequency. In the exemplary embodiment, the stimulating mechanism is at least one of a laser excitation UT source, a surface-mounted piezoelectric excitation UT source, and a water-coupled piezoelectric excitation UT source. Alternatively, the stimulating mechanism may be any UT source that enables the methods and systems to function as described herein. Moreover, in the exemplary embodiment, the UT source may be configured to transmit any wave mode that enables the methods and systems to function as described herein including, without limitation, longitudinal waves, shear waves, Lamb waves, and/or Rayleigh waves.

Figure 8:
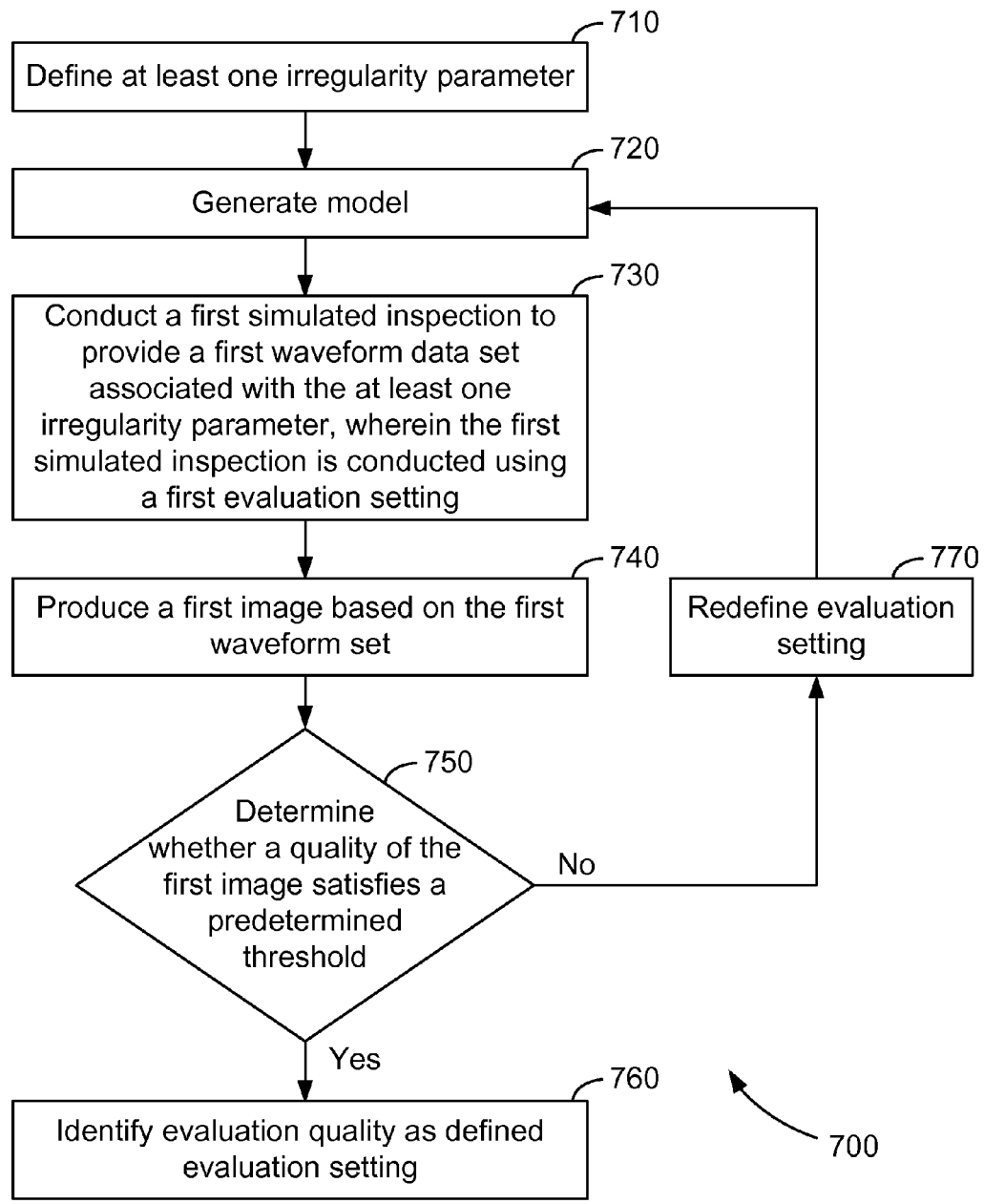
FIG. 8 is a flowchart of an exemplary method that may be implemented to inspect the composite structure shown in FIG. 2 using the computer system shown in FIG. 5.

FIG. 8 is a flowchart of an exemplary method 700 that may be implemented by computer system 500 to inspect composite structure 200 and/or irregularity 270. During operation, in the exemplary embodiment, at least one irregularity parameter is defined 710 by computer system 500 and/or a user. In the exemplary embodiment, the irregularity parameters may include an irregularity thickness 290, an irregularity width 300, an irregularity length, an irregularity location, and/or an irregularity shape. In the exemplary embodiment, a model is generated 720 based on the irregularity parameters, and an inspection of the model is conducted 730 to provide a waveform data set associated with the irregularity parameter and/or the model. More specifically, in the exemplary embodiment, the inspection of the model is conducted 730 using an evaluation setting associated with an ultrasonic testing (UT) source or stimulating mechanism defined by computer system 500 and/or the user.

In the exemplary embodiment, an imaging algorithm is applied to produce 740 a virtual image based on the waveform set, and it is determined 750 whether a quality of the virtual image satisfies a predetermined threshold. If the quality of the virtual image satisfies the predetermined threshold, in the exemplary embodiment, the evaluation setting is identified 760 as a desired evaluation setting for use in inspecting composite structure 200. If the quality of the virtual image does not satisfy the predetermined threshold, in the exemplary embodiment, another evaluation setting associated with the stimulating mechanism is defined 770 by computer system 500 and/or the user, and another model is generated 720 based on the irregularity parameters using the re-defined evaluation setting. For example, in the exemplary embodiment, the evaluation setting is re-defined using a finite element analysis. Alternatively, the evaluation setting may be re-defined using any method and/or process that enable the methods and systems to function as described herein. In the exemplary embodiment, method 700 is iteratively repeated until at least one desired evaluation setting is identified 760.

The embodiments described herein relate generally to non-destructive evaluation of materials and, more particularly, to methods and systems for use in inspecting a composite structure for irregularities. The embodiments described herein facilitate analytically and systematically obtaining ultrasonic responses associated with composite laminate layup structures. That is, the embodiments described herein use a finite element-based method to model composite structures at a detailed level to geometrically and/or physically characterize irregularities within the composite structure. As such, the embodiments described herein enable effectively and accurately understanding ultrasonic wave propagation within composite structures.

Exemplary embodiments of methods and systems for inspecting composite structures for irregularities are described above in detail. The methods and systems are not limited to the specific embodiments described herein, but rather, components of systems and/or steps of the method may be utilized independently and separately from other components and/or steps described herein. Each method step and each component may also be used in combination with other method steps and/or components. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for use in inspecting a composite structure, said method comprising:
    generating a virtual model of the composite structure;
    defining at least one irregularity parameter;
    conducting a first simulated inspection of the virtual model with a modeling module configured to transmit at least one simulated wave towards the virtual model to provide a first non-transitory waveform data set associated with the at least one irregularity parameter, wherein the first simulated inspection is conducted using a first evaluation setting that facilitates forming the at least one simulated wave;
    producing a first image based on the first non-transitory waveform data set;
    determining whether a quality of the first image satisfies a predetermined image quality threshold that would enable inspection of the composite structure for irregularities including wrinkles; and
    using the first evaluation setting to conduct a physical inspection of the composite structure with a stimulating mechanism if the first image satisfies the predetermined image quality threshold, wherein the stimulating mechanism uses the first evaluation-setting to transmit at least one physical wave towards the composite structure to detect irregularities in the composite structure.

2. A method in accordance with claim 1 further comprising identifying the first evaluation setting as an evaluation setting for use in conducting the physical inspection, wherein the first evaluation setting includes at least one of a stimulation source, a stimulation source beam width, a distance between the at least one stimulating mechanism and the composite structure, and a distance between the at least one stimulating mechanism and a sensor.

3. A method in accordance with claim 1 further comprising:
    conducting a second simulated inspection of the virtual model to provide a second non-transitory waveform data set associated with the at least one irregularity parameter, wherein the second simulated inspection is conducted using a second evaluation setting that is different from the first evaluation setting, wherein the quality of the first image does not satisfy the predetermined threshold;
    producing a second image based on the second non-transitory waveform data set;
    determining that a quality of the second image satisfies a predetermined threshold; and
    conducting the physical inspection also using the second evaluation setting.

4. A method in accordance with claim 1 further comprising generating at least one model based on the at least one irregularity parameter, wherein the model is a graphical representation of the at least one irregularity parameter.

5. A method in accordance with claim 1, wherein defining at least one irregularity parameter further comprises defining at least one irregularity parameter including at least one of an irregularity thickness, an irregularity width, an irregularity length, an irregularity location, and an irregularity shape.

6. A method in accordance with claim 1 further comprising defining at least one composite structure parameter including at least one of an outer ply thickness, an inner ply thickness, a number of plies, a ply layup, a composite structure thickness, a material used to fabricate at least a portion of the at least one composite structure, a number of element layers per ply, a resin thickness, and a resin density.

7. A method in accordance with claim 1 further comprising defining at least one stimulation parameter including at least one of a type of stimulating mechanism, a beam width, a wave mode, a relative orientation of at least one stimulating mechanism with respect to the composite structure, a distance between the at least one stimulating mechanism and the composite structure, a distance between the at least one stimulating mechanism and a sensor, an impulse shape and center frequency, a couplant, and a couplant thickness.

8. A computer-readable storage device having encoded thereon computer readable instructions that are executable by a processor to perform functions comprising:
conducting a first simulated inspection of a virtual model of a composite structure using a modeling module configured to transmit at least one simulated wave towards the virtual model to provide a first non-transitory waveform data set associated with at least one irregularity parameter, wherein the first simulated inspection is conducted using a first evaluation setting that facilitates forming the at least one simulated wave;
producing a first image based on the first non-transitory waveform set;
determining whether a quality of the first image satisfies a predetermined image quality threshold that would enable inspection of the composite structure for irregularities including wrinkles; and
identifying the first evaluation setting as an evaluation setting for use in conducting a physical inspection of the composite structure with a stimulating mechanism if the first image satisfies the predetermined image quality threshold; and
directing the stimulating mechanism, using the first evaluation setting, to transmit at least one physical wave towards the composite structure to detect irregularities in the composite structure.

9. A computer-readable storage device in accordance with claim 8, wherein the functions performed by the processor further comprise identifying the first evaluation setting as an evaluation setting for use in conducting the physical inspection, wherein the first evaluation setting includes at least one of a stimulation source, a stimulation source beam width, a distance between the at least one stimulating mechanism and the composite structure, and a distance between the at least one stimulating mechanism and a sensor.

10. A computer-readable storage device in accordance with claim 8, wherein the functions performed by the processor further comprise:
conducting a second simulated inspection of the virtual model to provide a second non-transitory waveform data set associated with the at least one irregularity parameter, wherein the second simulated inspection is conducted using a second evaluation setting that is different from the first evaluation setting, wherein the quality of the first image does not satisfy the predetermined threshold;
producing a second image based on the second non-transitory waveform data set;
determining that a quality of the second image satisfies a predetermined threshold; and
conducting the physical inspection using the second evaluation setting.

11. A computer-readable storage device in accordance with claim 8, wherein the functions performed by the processor further comprise generating at least one model based on the at least one irregularity parameter, wherein the model is a graphical representation of the at least one irregularity parameter.

12. A computer-readable storage device in accordance with claim 8, wherein the functions performed by the processor further comprise defining at least one irregularity parameter including at least one of an irregularity thickness, an irregularity width, an irregularity length, an irregularity location, and an irregularity shape.

13. A computer-readable storage device in accordance with claim 8, wherein the functions performed by the processor further comprise defining at least one composite structure parameter including at least one of an outer ply thickness, an inner ply thickness, a number of plies, a ply layup, a composite structure thickness, a material used to fabricate at least a portion of the at least one composite structure, a number of element layers per ply, a resin thickness, and a resin density.

14. A computer-readable storage device in accordance with claim 8, wherein the functions performed by the processor further comprise defining at least one stimulation parameter including at least one of a type of stimulating mechanism, a beam width, a wave mode, a relative orientation of at least one stimulating mechanism with respect to the composite structure, a distance between the at least one stimulating mechanism and the composite structure, a distance between the at least one stimulating mechanism and a sensor, an impulse shape and center frequency, a couplant, and a couplant thickness.

15. A system comprising:
an ultrasonic modeling module configured to transmit at least one simulated wave towards a virtual model of a composite structure to conduct a first simulated inspection of the virtual model such that a first non-transitory waveform data set associated with at least one irregularity parameter is provided, wherein the first simulated inspection is conducted using a first evaluation setting that facilitates forming the at least one simulated wave; and
a virtual imaging module configured to produce a first image based on the first non-transitory waveform data set, configured to determine whether a quality of the first image satisfies a predetermined image quality threshold that would enable a physical inspection of the composite structure for irregularities including wrinkles to be conducted, and configured to identify the first evaluation setting as a desired evaluation setting for conducting the physical inspection of a composite structure to detect irregularities in the composite structure if the first image satisfies the predetermined image quality threshold.

16. A system in accordance with claim 15 further comprising an evaluating module configured to identify the first evaluation setting as an evaluation setting for use in conducting the physical inspection, wherein the first evaluation setting includes at least one of a stimulation source, a stimulation source beam width, a distance between the at least one stimulating mechanism and the composite structure, and a distance between the at least one stimulating mechanism and a sensor.

17. A system in accordance with claim 15, wherein the ultrasonic modeling module is further configured to conduct a second simulated inspection of the virtual model to provide a second non-transitory waveform data set associated with the at least one irregularity parameter, the virtual imaging module is further configured to produce a second image based on the second non-transitory waveform data set, and determine that a quality of the second image satisfies a predetermined threshold, and the system further comprises an evaluating module configured to identify a second evaluation setting, wherein the second simulated inspection is conducted using the second evaluation setting that is different from the first evaluation setting, wherein the quality of the first image does not satisfy the predetermined threshold.

18. A system in accordance with claim 15, wherein the ultrasonic modeling module is further configured to generate at least one model based on the at least one irregularity parameter, wherein the model is a graphical representation of the at least one irregularity parameter.

19. A system in accordance with claim 15, wherein the ultrasonic modeling module is further configured to define at least one irregularity parameter including at least one of an irregularity thickness, an irregularity width, an irregularity length, an irregularity location, and an irregularity shape, and define at least one composite structure parameter including at least one of an outer ply thickness, an inner ply thickness, a number of plies, a ply layup, a composite structure thickness, a material used to fabricate at least a portion of the at least one composite structure, a number of element layers per ply, a resin thickness, and a resin density.

20. A system in accordance with claim 15, wherein the ultrasonic modeling module is further configured to define at least one stimulation parameter including at least one of a type of stimulating mechanism, a beam width, a wave mode, a relative orientation of at least one stimulating mechanism with respect to the composite structure, a distance between the at least one stimulating mechanism and the composite structure, a distance between the at least one stimulating mechanism and a sensor, an impulse shape and center frequency, a couplant, and a couplant thickness.

\* \* \* \* \*